(12) United States Patent
Beaumont et al.

(10) Patent No.: US 10,722,835 B2
(45) Date of Patent: Jul. 28, 2020

(54) METHOD AND DEVICE FOR THE REVERSIBLE ADSORPTION OF CARBON DIOXIDE

(71) Applicant: SKYTREE B.V., Amsterdam (NL)

(72) Inventors: Maximus Llewelyn Beaumont, Amsterdam (NL); Anthony Charles Thirkettle, Leiden (NL)

(73) Assignee: SKYTREE B.V., Amsterdam (NL)

( * ) Notice: Subject to any disclaimer, the term of this patent is extended or adjusted under 35 U.S.C. 154(b) by 232 days.

(21) Appl. No.: 15/509,951

(22) PCT Filed: Sep. 12, 2014

(86) PCT No.: PCT/EP2014/069569
§ 371 (c)(1),
(2) Date: Mar. 9, 2017

(87) PCT Pub. No.: WO2016/037668
PCT Pub. Date: Mar. 17, 2016

(65) Prior Publication Data
US 2017/0296961 A1    Oct. 19, 2017

(51) Int. Cl.
*B01D 53/04* (2006.01)
*B01J 20/28* (2006.01)
(Continued)

(52) U.S. Cl.
CPC ........... *B01D 53/0415* (2013.01); *A01G 7/02* (2013.01); *A01G 9/18* (2013.01); *A01G 33/00* (2013.01);
(Continued)

(58) Field of Classification Search
CPC .............. A01K 63/042; B01D 2256/22; B01D 2257/504; B01D 53/0415; B01D 53/0462; B01D 53/047; B01D 53/053; B01D 2253/202; B01D 2253/206; B01D 2253/306; B01D 2253/308; B01J 20/20; B01J 20/261; B01J 20/267; B01J 20/2805; B01J 20/28059; B01J 20/28052; B01J 20/28069; B01J 20/20878; B01J 20/2808; B01J 20/28083; B01J 20/28085;
(Continued)

(56) References Cited

U.S. PATENT DOCUMENTS 3,627,478 A    12/1971 Tepper
5,876,488 A *  3/1999 Birbara ............ B01J 20/321
                                                    96/111
(Continued)

FOREIGN PATENT DOCUMENTS

EP    1364698 A1    11/2003
WO    01/21269 A    3/2001

*Primary Examiner* — Frank M Lawrence, Jr.
(74) *Attorney, Agent, or Firm* — Nixon Peabody LLP; Ronald I. Eisenstein; Nicole D. Kling (57) ABSTRACT

The present invention relates to a device for the reversible adsorption of carbon dioxide from a gas mixture, comprising at least one adsorbent vessel comprising one or a plurality of gas permeable cartridge vessels of an inert and dimensionally stable material, and each cartridge comprising a suitable polymeric particular adsorbent having a primary amino functionality; to an arrangement including the device, and to a method for ad- and desorption of carbon dioxide.

23 Claims, 8 Drawing Sheets

(51) Int. Cl.
| | |
|---|---|
| *B01D 53/053* | (2006.01) |
| *B01D 53/047* | (2006.01) |
| *B01J 20/34* | (2006.01) |
| *B01J 20/20* | (2006.01) |
| *B01J 20/26* | (2006.01) |
| *C01B 32/50* | (2017.01) |
| *A01G 7/02* | (2006.01) |
| *A01G 9/18* | (2006.01) |
| *A01G 33/00* | (2006.01) |
| *A01K 63/04* | (2006.01) |
| *C12N 1/12* | (2006.01) |

(52) U.S. Cl.
CPC .......... *A01K 63/042* (2013.01); *B01D 53/047* (2013.01); *B01D 53/0462* (2013.01); *B01D 53/053* (2013.01); *B01J 20/20* (2013.01); *B01J 20/261* (2013.01); *B01J 20/267* (2013.01); *B01J 20/2805* (2013.01); *B01J 20/2808* (2013.01); *B01J 20/28052* (2013.01); *B01J 20/28059* (2013.01); *B01J 20/28069* (2013.01); *B01J 20/28078* (2013.01); *B01J 20/28083* (2013.01); *B01J 20/28085* (2013.01); *B01J 20/3425* (2013.01); *B01J 20/3441* (2013.01); *B01J 20/3458* (2013.01); *B01J 20/3483* (2013.01); *B01J 20/3491* (2013.01); *C01B 32/50* (2017.08); *C12N 1/12* (2013.01); *B01D 2253/202* (2013.01); *B01D 2253/206* (2013.01); *B01D 2253/306* (2013.01); *B01D 2253/308* (2013.01); *B01D 2256/22* (2013.01); *B01D 2257/504* (2013.01); *B01J 2220/62* (2013.01); *C01B 2210/0015* (2013.01); *C01B 2210/0021* (2013.01); *Y02C 10/08* (2013.01); *Y02P 60/247* (2015.11)

(58) Field of Classification Search
CPC ................ B01J 20/3425; B01J 20/3441; B01J 20/3458; B01J 20/3483; B01J 20/3491; B01J 20/222; B01J 20/62; C01B 2210/0015; C01B 2210/0021; C01B 32/50; C12N 1/12; Y02C 10/08; Y02P 60/247
USPC ...... 95/96, 106, 115, 139, 148; 96/121, 126, 96/130, 131, 136, 144, 146; 423/230
See application file for complete search history.

(56) References Cited

U.S. PATENT DOCUMENTS

| | | | |
|---|---|---|---|
| 6,322,612 B1* | 11/2001 | Sircar | B01D 53/047 95/104 |
| 6,402,809 B1* | 6/2002 | Monereau | B01D 53/0462 95/105 |
| 7,288,136 B1* | 10/2007 | Gray | B01D 53/1475 95/139 |
| 7,767,004 B2* | 8/2010 | Sayari | B01D 53/02 95/285 |
| 8,500,854 B1* | 8/2013 | Pennline | B01D 53/0462 95/117 |
| 2007/0028764 A1* | 2/2007 | Wittrup | B01D 53/0454 95/8 |
| 2008/0087165 A1* | 4/2008 | Wright | B01D 53/04 95/51 |
| 2012/0228553 A1* | 9/2012 | Tirio | B01D 53/02 252/373 |
| 2014/0123850 A1* | 5/2014 | Bedell | B01J 20/3475 95/148 |

* cited by examiner

METHOD AND DEVICE FOR THE REVERSIBLE ADSORPTION OF CARBON DIOXIDE

CROSS REFERENCE TO RELATED APPLICATIONS

This application is a 371 National Phase Entry of International Patent Application No. PCT/EP2014/069569 filed on Sep. 12, 2014, the content of which is incorporated herein by reference in its entirety.

FIELD OF THE INVENTION

The subject invention relates to a method and a device for the reversible adsorption of carbon dioxide from a gas mixture.

The invention relates to a regenerative system comprising an adsorbent for capturing carbon dioxide reversibly from a gas stream, including ambient air.

Presently applied processes for the adsorption and desorption of carbon dioxide typically focus on gas streams with higher concentrations thereof, e.g. flue gases from industrial and energy production processes, such as for instance integrated gasification combined cycle (IGCC) processes. Herein, typically fluid components are employed which are contacted with the gas mixture, and are energy intensive, and/or driven by the comparatively high carbon dioxide concentrations. Typically these processes also remove other gaseous components from flue gases, such as nitrogen and sulphuric oxides. The thus obtained carbon dioxide may be separated off and typically is then pressurized for storage and use; however it typically contains impurities that are difficult to separate off.

Where solid adsorbent materials with functionalized surfaces are used for carbon dioxide adsorption, it is usually contained in a closed system, such as a flue stacks. In the case of air recycling systems for confined spaces, such as offices, submarines and spacecraft, the material is held in a packed bed form and fed with pressurized gas.

Alternatively, bottled carbon dioxide is available from companies that are producing bottled gases through separation of air, typically using large scale cryostatic air liquefaction processes. Again, typically the products include concentrated solid and bottled liquid carbon dioxide, typically of high quality. However, the liquefaction processes consume a tremendous amount of energy, additional to the transport costs and energy use for storage and transport to a suitable user.

Conversely, a major use of the carbon dioxide is in the production of plants in greenhouses, and increasingly, also for the production of microalgae in photo-bioreactors, for fuels and products derived therefrom.

However, the above-described carbon dioxide production processes are typically located in industrial areas that are remote from those of the potential application, adding costs for transport of bottled carbon dioxide, or requiring the installation of pipelines that are expensive and difficult to maintain.

At the same time, greenhouse owners are known to often burn natural gas or even coal and to use the flue gas mixture to increase the growth of the plants in the greenhouses, since the costs for this are lower than those for bottled carbon dioxide, despite the negative environmental impact. Furthermore, components of the flue gas mixture may very well negatively affect plant growth.

Accordingly, there remains a need for a process that can efficiently and with low energy consumption, generate a gas mixture comprising carbon dioxide in a higher concentration than in ambient air, preferably also without comprising noxious components.

Recently, processes using solid amine adsorption to capture atmospheric carbon dioxide have been reported. WO-A-2010/091831 for instance discloses a structure composed of fibre filaments wherein the fibre material is carbon and/or polyacrylonitrile and containing a sorbent with amine groups that is capable of a reversible adsorption and desorption cycle for capturing $CO_2$ from a gas mixture.

WO-A-2007/016271 and WO-A-2008/131132 discloses methods for removing carbon dioxide from a gas stream, comprising placing the gas stream in contact with a tertiary or quaternary ammonium functionalised resin placed in a roll-geometry chamber or a plurality of roll-geometry chamber connected in series, wetting the resin with water, collecting water vapour and carbon dioxide from the resin, and separating the carbon dioxide from the water vapour.

US20110296872 discloses a process for removing carbon dioxide from a gas stream, comprising contacting the gas stream with a solid inorganic sorbent substrate comprising an immobilized ammonium functionalised inorganic material as sorbent, and releasing the carbon dioxide subsequently. The disclosed process has the issue of achieving a suitable adsorption and flow rates through the sorbent substrate, while also having to move the substrate to release the carbon dioxide.

WO00/02643 discloses a process for removing carbon dioxide from closed or semi-closed aircraft or submarine cabins, using one or more parallel bed of beads of an ionic exchange resins having benzylamine groups for removal of carbon dioxide from closed or semi-closed space-, aircraft or submarine cabins; whereby the regeneration can only take place once there is access to outside air, without the issue of toxicity of the released carbon dioxide.

Applicants now have found a process and a device for executing the process that provides gas mixtures having an increased carbon dioxide level, which permits to operate at a higher carbon dioxide yield, and with significantly lower energy use.

The subject process and device permits to produce gas mixtures having an increased carbon dioxide level without the need for using highly pressurized equipment and/or cryostatic devices at lower financial expenditure than other known air-capture processes. It also has a lower volume requirement, higher stability; creates no perceptible odours such as typically the case when quaternary amines were to be used, and offers at least an equal or higher $CO_2$ capture performance with respect to weight and more practical than present processes using solid or liquid adsorbents.

SUMMARY OF THE INVENTION

Accordingly, in a first aspect, the present invention relates to a device for the reversible adsorption of carbon dioxide from a gas mixture, comprising at least one adsorbent vessel comprising a plurality of gas permeable cartridge vessels of an inert and dimensionally stable material, and each cartridge comprising a suitable polymeric particular adsorbent having a primary amino functionality at a total capacity of at least 2.0 eq./l, a surface area (BET) in the range of from 25 to 75 $m^2/g$, and an average pore diameter of 0.01 to 0.25 mm, and further comprising a means for: desorption of the absorbed carbon dioxide by pressure, humidity and/or temperature absorption swing, and means for directing the desorbed gas mixture from the adsorbent cartridges.

In a second aspect, the subject invention relates to an arrangement for the enhancement of plant growth, comprising a device according to any one of the preceding claims, and further comprising means for distributing the desorbed carbon dioxide, such as a gas duct, and/or a sparger.

The term "sparger" herein may be any suitable means for the distribution of gas, including ceramic or metal diffusers for aquatic use.

In yet a further aspect, the present invention relates to a process for separating carbon dioxide from a gas mixture by a pressure, temperature and/or humidity swing adsorption-desorption process, comprising the steps of: (a) in an adsorbent vessel comprising a plurality of gas permeable cartridge vessels of an inert and dimensionally stable material, contacting the gas mixture with at least one polymeric particular adsorbent having a primary amino functionality at a total capacity of at least 2.0 eq./l, a surface area (BET) in the range of from 25 to 75 $m^2/g$, and an average pore diameter of 0.01 to 0.25 mm, and at a pressure $P_1$, a humidity $H_1$ and a temperature $T_1$ until a desired amount of carbon dioxide is adsorbed onto the adsorbent, and (b) desorbing at least part of the carbon dioxide adsorbed in step (a), to produce a stream enriched in carbon dioxide at a total pressure $P_2$ and/or a temperature $T_2$, and/or at a humidity level $H_2$, at which temperature and/or pressure the carbon dioxide has a lower adsorption constant with respect to the adsorbent and therefore at least in part desorbs.

BRIEF DESCRIPTION OF THE FIGURES

These and further features can be gathered from the claims, description and drawings and the individual features, both alone and in the form of sub-combinations, can be realized in an embodiment of the invention and in other fields and can represent advantageous, independently protectable constructions for which protection is hereby claimed. Embodiments of the invention are described in greater detail hereinafter relative to the drawings, wherein:

The reference numbers are collated in Table 1:

TABLE 1

| Reference numerals |
|---|
| 1 Solar heat |
| 2 Represents ambient air, gas stream & heating fluid |
| 3 Concentrated $CO_2$ |
| 4 Material cartridges |

TABLE 1-continued

| Reference numerals |
|---|
| 5 Material enclosure (sealable) |
| 6 Heat, air and/or water recuperation |
| 7 Cartridge enclosing material |
| 8 Permeable membrane with minimum pore diameter |
| 9 Cartridge width optimized for atmospheric adsorption (5-50 mm) |
| 10 Cartridge spacing optimized for adequate air convection (10-100 mm) |
| 11 Cartridge stacking optimizing unit volume |
| 12 Closed greenhouse |
| 13 $CO_2$-capture unit |
| 14 Ambient atmospheric $CO_2$ |
| 15 Concentrated $CO_2$ supply |
| 16 Power & low heat |
| 17 Closed greenhouse vent transporting air with higher concentration $CO_2$ out of greenhouse to the natural environment after venting it first through the air-capture unit |
| 18 Mesh |
| 19 Sorbent |
| 20 Frame |
| 21 Heater wire |
| 22 Power contacts |
| 23 Sparger |
| 24 PCB Controller |
| 25 Micro-Pump |
| 26 Simple user controls |
| 27 Enclosed volume |
| 28 Actuator |
| 29 Cartridge with wire heater (xn) |
| 30 Ambient air |
| 31 Storage buffer |

DETAILED DESCRIPTION OF THE INVENTION

The present invention relates to carbon dioxide capture from a gas mixture, preferably ambient air, which could provide current and future users of carbon dioxide with a sustainable, on-site source of carbon dioxide offering greater supply reliability and location flexibility. The technology may advantageously be employed for enhancing plant growth in e.g. greenhouses for food or energy plants, or decorative purposes such as flowers; for biofuel or neutraceutical production through microalgae, and for other applications such as in the beverage industry, for storage under carbon dioxide, for medical applications and so on.

The subject process and device are in particular suitable for the fertilization by carbon dioxide enrichment of a greenhouse environment, where the process can increase crop yields and thus revenue, by up to 40%.

Further advantages of the carbon dioxide process according to the invention when used in greenhouses or other applications with respect to the traditional carbon dioxide sources include greater reliability of $CO_2$ supply;

greater location flexibility for greenhouse not having to consider a fixed $CO_2$ source; a $CO_2$ mixture without contaminants detrimental to plant growth; more control over $CO_2$ supply given to the greenhouse operator; and the possibility to use sustainable air-captured $CO_2$ as a marketing tool to enhance sales of the greenhouse crop.

A particularly useful application of the present invention relates to a method and apparatus for supplying carbon dioxide to vivaria, such as terraria and aquaria. More particularly, it relates to a carbon dioxide production and delivery apparatus and related method to increase the carbon dioxide concentration in aquaria, to promote photosynthesis and plant growth.

It is well known that during photosynthesis plants absorb carbon dioxide from the surrounding medium and convert it into simple carbohydrates, utilising the sun's energy, whilst releasing oxygen.

This process is essential for the survival and growth of the plant. The rate of photosynthesis is affected, amongst other factors, by the availability of carbon dioxide in the surrounding medium. A higher concentration of carbon dioxide will lead to an increased rate of photosynthesis, whilst a low carbon dioxide concentration will severely retard the rate of photosynthesis.

Aquatic plants require dissolved carbon dioxide in the surrounding water to enable them to grow. The concentration of carbon dioxide in the water is limited, in part, by the surface area of the water that is in contact with a carbon dioxide supply, such as the atmosphere, and the volume of water in which carbon dioxide can dissolve. The same logic applies to other types of closed vivaria that require specific environmental conditions, e.g. containers enclosed to keep an ecosystem alive. The term "vivarium" herein relates to tanks, pools or otherwise containers essentially filled with water for keeping live fish and other aquatic aerobic animals, including storage tanks; and to terraria, i.e. enclosures for keeping and raising living animals and plants and observing them under natural conditions. Examples include enclosed miniature gardens for e.g. tropical plants such as orchids or ferns, whereby these are typically in a closed sun-light transparent environment, permitting percolation of water vapour gas streams, thereby creating self-sustained ecosystems.

Oceans, rivers or lakes have relatively large surface areas and volumes with regard to the few photosynthetic organisms, aquaria typically offer only a relatively small surface area, yet typically contain a high proportion of plant matter. This necessitates a relatively high concentration of carbon dioxide in the water to enable the plants to thrive. Furthermore, the maintenance of aquatic organisms often requires specific environmental conditions, including important parameters such as water temperature, pH, presence of salts and amount of dissolved gases, including oxygen and carbon monoxide and dioxide.

The potential for the growth and proliferation of certain aquatic life forms also may require presence of flora and fauna specific to the natural habitat besides the presence of appropriate nutrients. Hence, there is a general trend to encourage growth of certain plant species in aquaria, also due to the photosynthetic oxygen production, thus creating a better environment for aquatic aerobic organisms, as well as for aesthetic reasons. Typically, carbon dioxide concentration of aquarium water is maintained at a high level in order to encourage plant growth, and thereby also helps to maintain the dissolved oxygen concentration. Presently employed systems tend to either utilise compressed carbon dioxide from compressed gas cylinders. This solution requires high-pressure reducing valves and high-pressure tubing, which is impractical for the average aquarium owner, due to the high capital expenditure and high maintenance costs, and regular replacement of empty gas bottles. An alternative to such systems uses the carbon dioxide released by fermentation from e.g. sugar by yeasts to produce $CO_2$, which is then introduced into the aquarium.

The present invention relates to a device for the provision of atmospheric carbon dioxide to vivaria, and in particular to aquaria, which does not require the use of compressed gas, or confined carbon dioxide generating species.

Accordingly, it is also an object of the present invention to provide a system capable of producing and safely dissolving carbon dioxide into aquaria, whilst avoiding the problems of the presently employed systems.

Furthermore, it is an object of the present invention to provide a system capable of controllably introducing carbon dioxide into aquarium water selectively.

The invention therefore relates to a regenerative a carbon dioxide production and delivery apparatus for aquaria comprising an adsorbent for capturing carbon dioxide reversibly from a gas stream, including ambient air, the apparatus comprising an adsorption/desorption device capable of producing a carbon dioxide enriched gas stream, a distribution means capable of introducing carbon dioxide or air into an aquarium through which the carbon dioxide is delivered into the aquarium.

The invention thus relates to a device for the adsorption of carbon dioxide from a gas stream on an adsorbent that is suitable for the regenerative adsorption of carbon dioxide, further comprising means for desorbing the carbon dioxide and a subsequent supply of the desorbed carbon dioxide to an aquarium, comprising means for the supply of the carbon dioxide enriched gas stream to an aquarium to form at least in part dissolved carbon dioxide.

Preferably, the regeneration of the adsorbent may be done by heat, more preferably by heating the saturated adsorbent electrically.

The present invention makes use of a reversible adsorption and desorption process, wherein the adsorbent composition can be regenerated, i.e. the absorbed carbon dioxide can be released again, through for instance temperature, humidity and/or pressure swing.

Different adsorbents may be employed according to the required circumstances. For the supply of carbon dioxide to e.g. aquaria, the adsorbent may be any suitable adsorbent that allows for regenerative adsorption and desorption under the mild conditions as employed. Typical adsorbents are solids, typically with an amine functionality, such as inorganic or organic polymeric components with sufficiently high surface areas per volume, e.g. zeolites, alumina, silica, silica alumina, and organic polymers, such as light and proporus beads or membranes.

Examples include zeolites, also referred to as molecular sieves; ceramic based materials eg. alumina, alumina-silica; titania; activated carbon, all of which may be midified by sutiable amines, e.g. Diethanolamine (DEA) or Polyethylenimine (PEI); or divinylbenzene based materials, or ethylenediamine-modified silica gels While the inorganic materials typically excel in high physical strength, the modification and regeneration conditions require high temperature and pressure, due to e.g. high heat capacity, which makes the often unsuitable for household use, or applications under mild conditions.

Activated carbon may be employed, e.g. DEA embedded activated carbon; however, it was found that this compound is not has sufficiently stable for a prolonged use, as it showed degradation under room conditions after two months.

The present process preferably makes use of a particular adsorbent having primary amino functionality, e.g. benzyl amine, as this was found to be most effective, and highly stable. Such materials have wide spread use as ion-exchange resins in bead form. Typical uses are in waste treatment and water purification. The resins can be produced in the form of beads or membranes, the latter including beads with a particular particle size distribution, dependent on the manufacturing process.

The polymeric beads can be functionalized to act as ion exchangers or absorbers/adsorbers for certain molecules. Typically, they are held in a pack bed configuration in a closed system, and used as a filter medium. After completing their purification/capture task, they are usually regenerated by washing with a solution or by applying heat.

Applicants found that a particularly suitable adsorbent for the present process and device is a polymeric particular adsorbent having a primary amino functionality at a total capacity of at least 2.0 eq./l, a surface area (BET) in the range of from 25 to 75 $m^2/g$, and an average pore diameter of 1 to 200 nm, more preferably of from 5 to 150 nm.

The surface area may preferably be determined according to Brunauer-Emmett-Teller (BET) Surface Area Determination—Test Method-BS 4359-1:1996 (ISO 9277:1). The total capacity and other properties may preferably determined according to test method ASTM D2187-94.

A particularly preferred adsorbent is a free base amine bead functionalized with the primary amine benzylamine and supported on a porous polyester structure crosslinked with divinyl benzene. The adsorbent preferably is in the form of spherical beads, which are functionalised with benzyl amine groups. The polymeric matrix hence comprises crosslinked polystyrene. It preferably has an activity expressed as total capacity of at least 2 eq./l, more preferably at least 2.1 and yet more preferably at least 2.2. It preferably has a uniformity coefficient of at most 1.9, more preferably at most 1.8.

The beads preferably have a size in the range of from 0.25 to 1.5 mm, more preferably 0.3 to 1.3 mm, for at least 85% of the particles present. The adsorbent preferably has a bulk density of 600 g/l to 720 g/l, with a variation of +/−5%.

The water retention rate preferably is in the range of from 60 to 75 wt. %, more preferably in the rage of from 65 to 70 wt. %.

The adsorbent surface area (BET) preferably is in the range of from 30 to 65 $m^2/g$, more preferably 40 to 60, and most preferably 45 to 55 $m^2/g$.

The pore volume preferably is in the range of from 0.2 to 0.4 $cm^3/gm$. The adsorbent preferably has an average pore diameter of 25 nm.

The adsorbent is placed in one or more media containing elements, further referred to as cartridges herein. The adsorbent preferably is in a lose configuration, i.e. not a packed bed configuration, to permit the gas mixture to circulate through the adsorbent without the need for significantly pressurizing the fed gas mixture.

The cartridge further comprises a gas permeable membrane or division having an average pore diameter in the range of from 0.01 to 0.25 mm to allow the gas mixture ample access to the adsorbent particles, while maintaining the adsorbent particles in place. The cartridges may further comprise additional means to keep the adsorbent in place, e.g. they can be in the shape of stepped bags, or maintain corrugated structures, provided these do not negatively influence the diffusion of the gas mixture through the adsorbent particles or beads.

The adsorbent may also be employed in a different manner, e.g. it may come in the form of beads buts also other shapes eg. cylinders, sheets, solid blocks may be useful, provided that they provide the surface area and activity as required. Blocks might be prepared for instance by processes include injection molding.

Preferably, independently from the actual shape chosen, the cartridges have a thickness in the direction of the flow of the gas mixture in the range of from 5 mm to 50 mm, and are spaced apart in distance sufficient to allow for the adequate diffusion of atmospheric carbon dioxide between them.

Applicants found that the thickness of the cartridges was relevant for the adsorption speed, and largely independent from various low gas flow speeds. A higher thickness no longer permitted to have adsorption/desorption cycles useful for industrial processes, which preferably are in the range of from 2 to 24 hours if working under ambient conditions.

The actual gas flow rates are preferably in the range of from 0.1 to 15 m/s, more preferably in the range of from 0.5 to 5 m/s. The actual the shape and thickness of the cartridges may be adjusted according to the desired adsorption-desorption regeneration cycle, which preferably is in the range of from 2 to 24 hours.

Preferably, the cartridges are placed sequentially with respect to the direction of the gas mixture.

The device according to the invention further preferably comprises means for the supplying the gas mixture to the cartridges.

The device advantageously allows the use of low grade heat sources, more preferably renewable or sustainable heat sources, e.g. geothermal energy, solar energy or industrial waste heat for the desorption.

The heat may be applied to the device via a heat exchanger or even by direct or indirect solar irradiation, where suitable. During the regeneration, i.e. desorption process, a suitable construction like a reverse valve, or other means of sealing the device from the ambient air flow may be applied in order to capture the released carbon dioxide.

The desorption process is preferably done by a fluid, e.g. a gas stream such as air, water vapour, or water purging the adsorbent, preferably at atmospheric or reduced pressure. This fluid stream may also be used to heat up the system for the desorption process before and after entering the structure.

The present device and process is particularly suitable for producing rather carbon dioxide enriched gas streams, such as air, containing of from 1% to 99.99% of carbon dioxide, which is for example in the range demanded by greenhouse operators who fertilize their plants with higher carbon dioxide concentrations.

Preferably, the device according to the invention further comprises means for desorption of the adsorbed carbon dioxide by pressure, humidity and/or temperature adsorption swing, and means for directing the desorbed gas mixture from the adsorbent cartridges.

The device and process preferably operate at a pressure in the range of from 0.05-1.5 bar, more preferably of from 0.1-1.3 bar.

The device and process preferably operate at a temperature of from −20 to 150° C., preferably in the range of from 0 to 120° C., yet more preferably 10 to 100° C.

Preferably, the device according to the invention further comprises a means for recuperation of heat and/or fluids, and a desorbed gas mixture. Preferably, the device according to the invention further comprises a means for measuring the carbon dioxide adsorption level and/or gas flow rates.

Preferably, the device according to the invention comprises a means for contacting the adsorbent with a warm fluid for inducing desorption of the carbon dioxide.

Preferably, the device according to the invention also comprises an arrangement to subject the cartridges to reduced pressure, and subsequently to contact the cartridges with water having a temperature in the range of from 60° C. to 100° C., and means for separating water or water vapour from the released carbon dioxide for recycling to arrangement.

Preferably, in the device according to the invention, one or more cartridges are arranged sequentially and/or parallel such that one or more cartridges can be removed for replacement and/or maintenance of any cartridge without having to stop the adsorption process.

The present invention further relates to an arrangement also comprising a green house for higher plants, or a photo bioreactor for microalgae growth.

The arrangement preferably comprises a low grade energy provision means, preferably a renewable source of heat, as set out above.

In the process according to the invention, step (b) includes contacting the cartridges with a fluid at a temperature in the range of from 60° C. to 100° C., and optionally, optionally at a reduced pressure. Preferably, the fluid is water or air.

Alternatively, step (b) includes heating the adsorbent material in a cartridge directly. This may advantageously be done by having heating means present in the cartage, e.g. metal wires or foils that are electrically heatable by resistance or induction. Preferably these are made from a suitable material which is inert towards the adsorbent material and the formed carbon dioxide. Examples for such materials include is palladium, platinum, nickel, cobalt, chrome, and/or iron wires, or alloys thereof such as Ni/Chr.

The temperature required fore a suitbale release depends on the material to be employed, but generally should not be reach a temperature whereby the adsorbent starts to release amine or starts retropolymerisation. A lower temperature applied, e.g. heating the adsorbent to a temperature of from 60° C. to 80° C. will allow for more cycles without adsorbent deactivation or decomposition as compared to heating to temperatures above 150° C.

The process preferably comprises alternating steps (a) and (b) in a pattern of between 2 minutes and 2 days, more preferably between 30 minutes and 24 hours. Preferably, the flow of the gas mixture for step (b) is reversed, the temperature increased. Where a constant flow is desired, this may advantageously be achieved by the use of a buffer, whereby the carbon dioxide amount released into the final application can be kept constant, or by a using more than one cartridge in parallel, however different stages of the cycle.

For aquatic applications such as aquaria, the present invention has the benefit that the amount of carbon dioxide released, and thus present in an aquarium can be readily regulated by the amount of air that is removed from the adsorbent upon regeneration conditions, e.g. upon heating. This allows a number of highly relevant conditions to be achieved in the volume of an aquarium by simple flow and temperature controls, and therefore makes the subject process and apparatus in particular valuable for this application.

Accordingly, the present invention also relates to the use of the apparatus and process for the control the pH of a given aqueous environment. The control of the pH by simple addition of carbon dioxide at a predetermined flow and amount allows for instance the control of the water quality of fish ponds and fish installations, such as e.g. fish farms or koi ponds, whereby the quality of the fish, shrimp or koi is safeguarded. Kois (*Cyprinus carpio carpio*) tend to get stains from too high or too low pH, which is detrimental for their value, while fish farms need different, however controlled conditions for the fish larvae, or later stages of the fish's development.

A further use is the provision of carbon dioxide for the formation of calcium carbonate in salt water ponds, e.g. for colony forming aquatic life forms, such as a corals, or for the formation of the exoskeletons of diatomic microalgae.

The control of the pH of the water may also be employed to control the water quality in closed systems, e.g. the drink or use water piping on large marine vessels, such as cruise ships or airplane carries. These presently typically employ high pressured carbon dioxide canisters that need to be exchanged on regular instances, for the control of the water in the ships piping.

The process preferably comprises step (c) of directing the released gaseous stream comprising the desorbed carbon dioxide to a desired application, including a green house, a (micro) algae photo incubator, a beverage plant, and/or a storage facility.

The system may advantageously also include a storage buffer. Preferably the storage buffer comprises to store an amount of carbon dioxide enriched gas mixture as required for of from 0.1 to 2 days $CO_2$ usage for a particular application. The buffer can either hold the $CO_2$ gas in a compressed form, or by taking advantage of a solid storage structure such as Activated Carbon or a Metal Organic Framework.

The present invention also relates to the use of the subject device, arrangement and process for use in air-conditioning/ventilation applications, whereby carbon dioxide can be removed from confined spaces such as buildings, offices, hotel rooms, schools, air planes, submarines, high speed trains, and the likes, whether with or without pressurized cabins.

It furthermore relates to carbon dioxide supply for laboratories/scientific equipment and/or medical facilities, where presently compressed gas is employed.

Experimental Part

The following non-limiting examples illustrate the usefulness of the present invention.

EXAMPLE 1

Adsorption Test

A round cartridge was loosely filled with adsorbent material, which was held in a container between two layers of mesh, at a thickness of 1 cm. The adsorbent material was a primary amino functional ion exchange resin (a dinvinyl benzene based polymeric particular adsorbent having a primary amino functionality at a total capacity of at least 2.0 eq./l, a surface area (BET) in the range of from 25 to 75 $m^2/g$, and an average pore diameter 5 to 150 nm) and held between two layers of appropriately pored metal mesh was placed in an airtight sealable container. The container was linked to a vacuum pump, and a carbon dioxide sensor measuring out-coming gas streams. Temperature and humidity as well as carbon dioxide concentration were measured by suitable sensors throughout the test.

The adsorbent was exposed by opening the container allowing for natural diffusion of $CO_2$ into the material. It was then heated up to 60° C. to 100° C.

Figure 1:
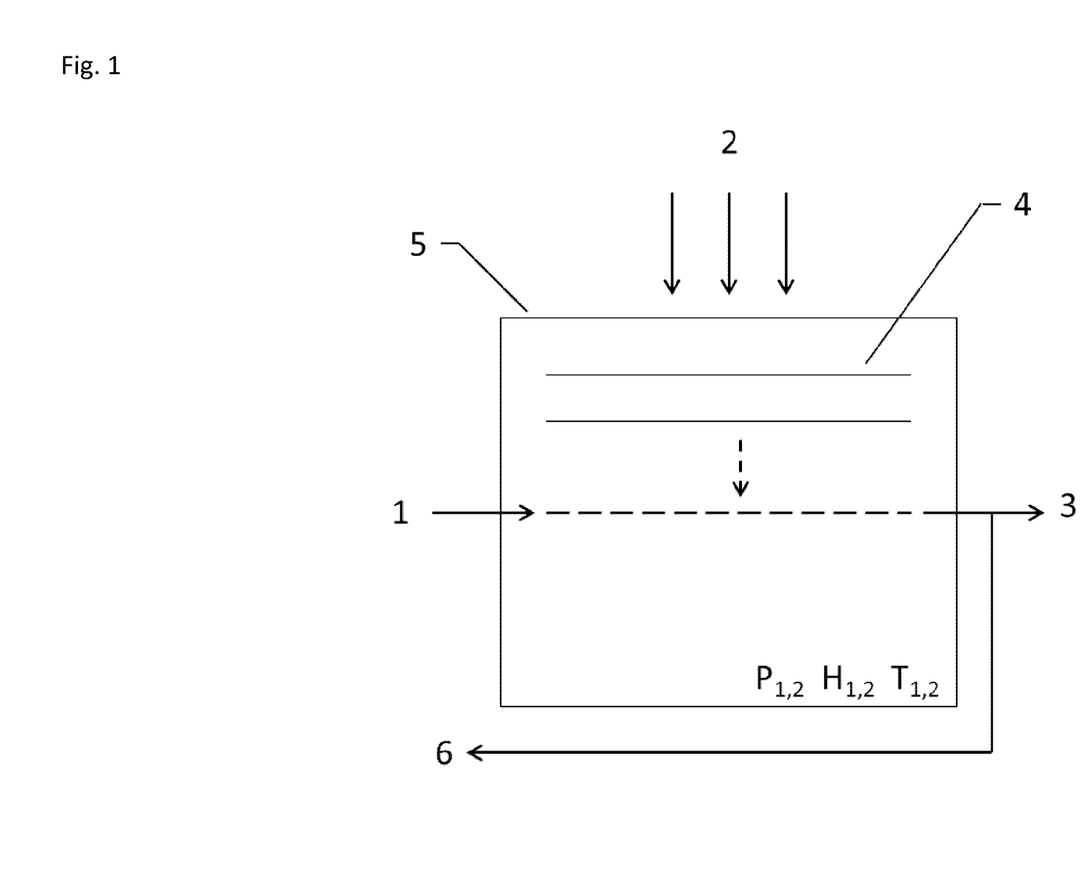
FIG. 1 discloses a schematic view of the above described process which comprises of three main elements: the cartridges, a sealable enclosure volume to house the cartridges and process related energy and fluid flows.
Figure 2:
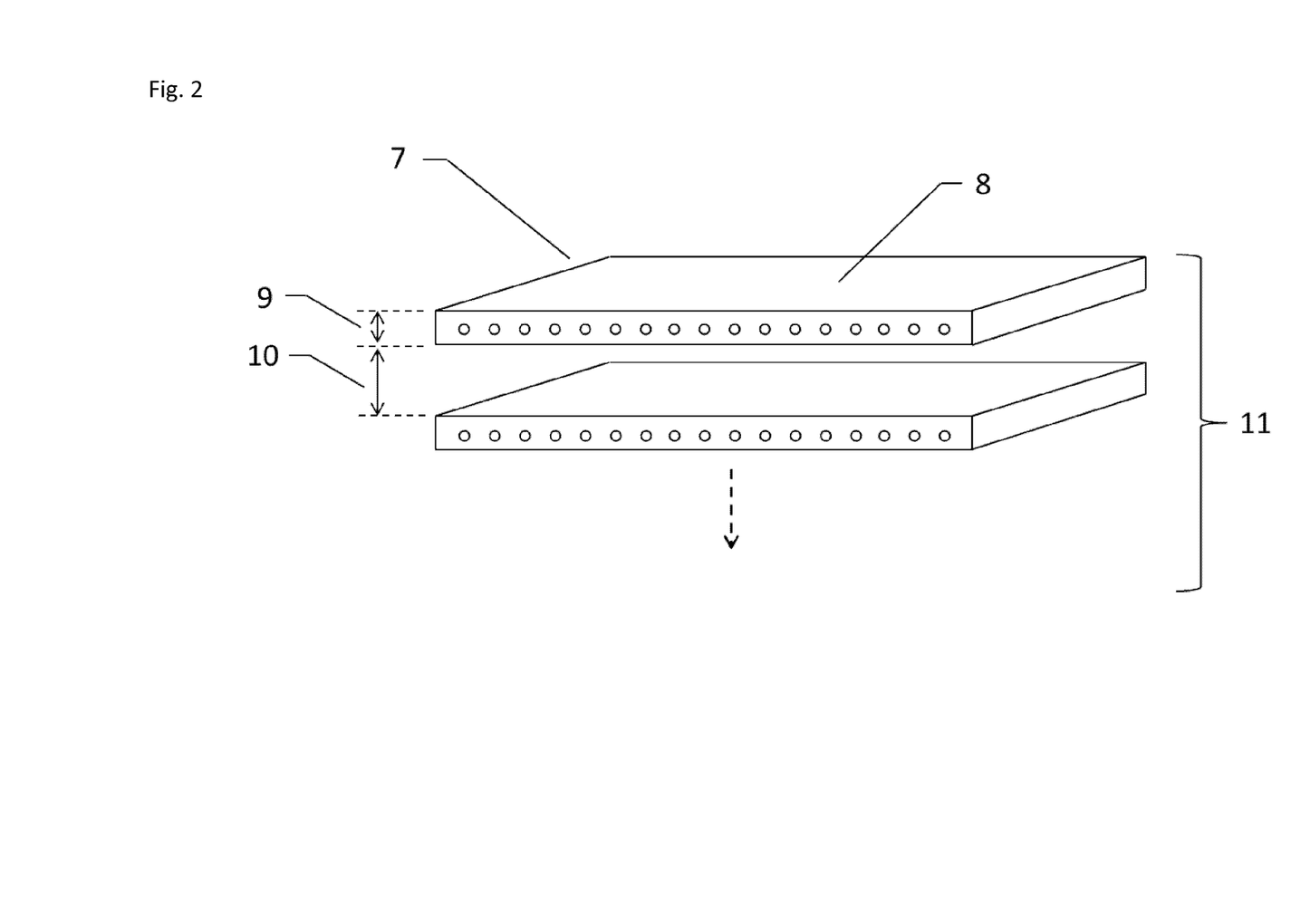
FIG. 2 discloses a representation of an adsorbent stack comprising a preferred cartridge thickness and cartridge spacing optimized for ambient atmospheric CO2 capture.
Figure 3:
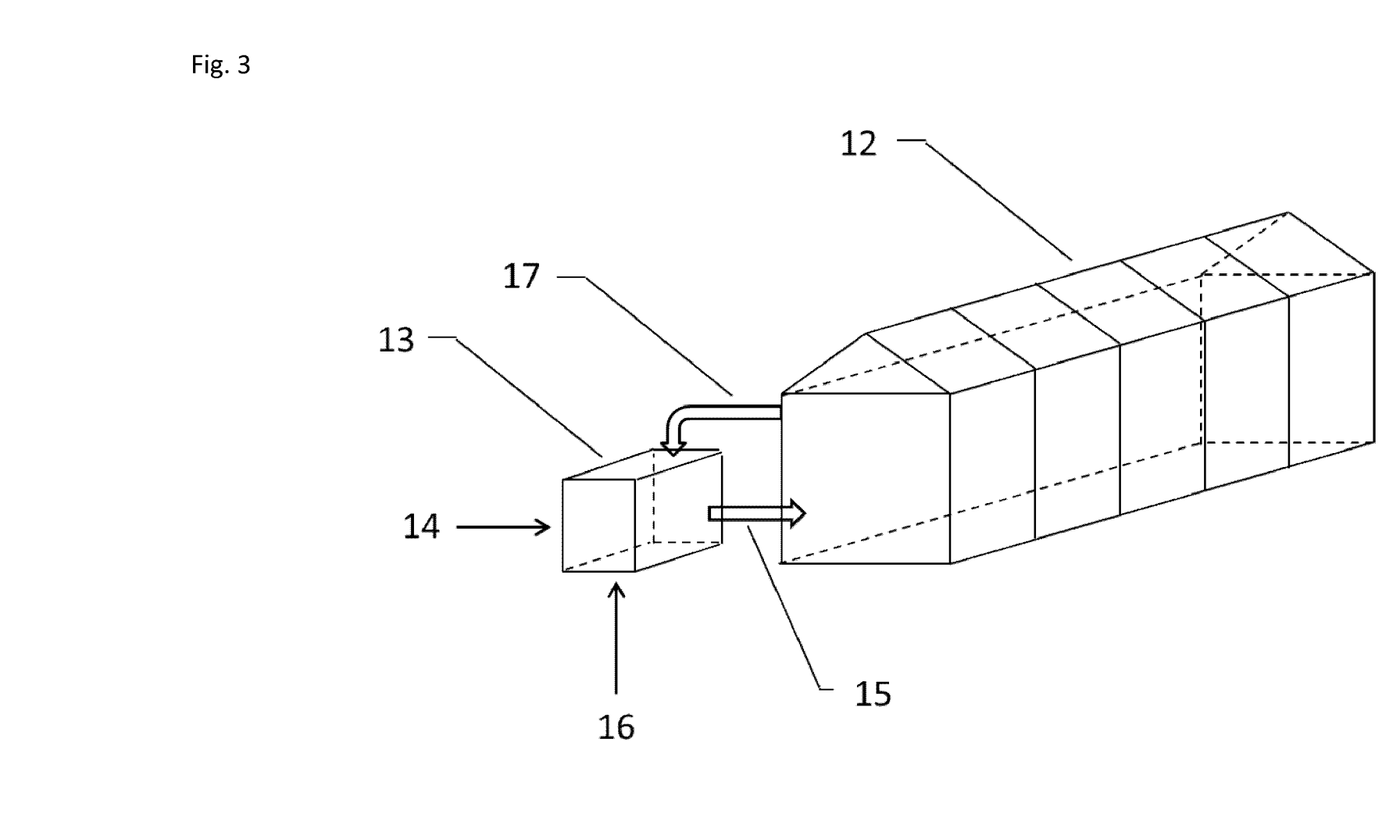
FIG. 3 shows a schematic overview of a preferred arrangement.
Figure 4:
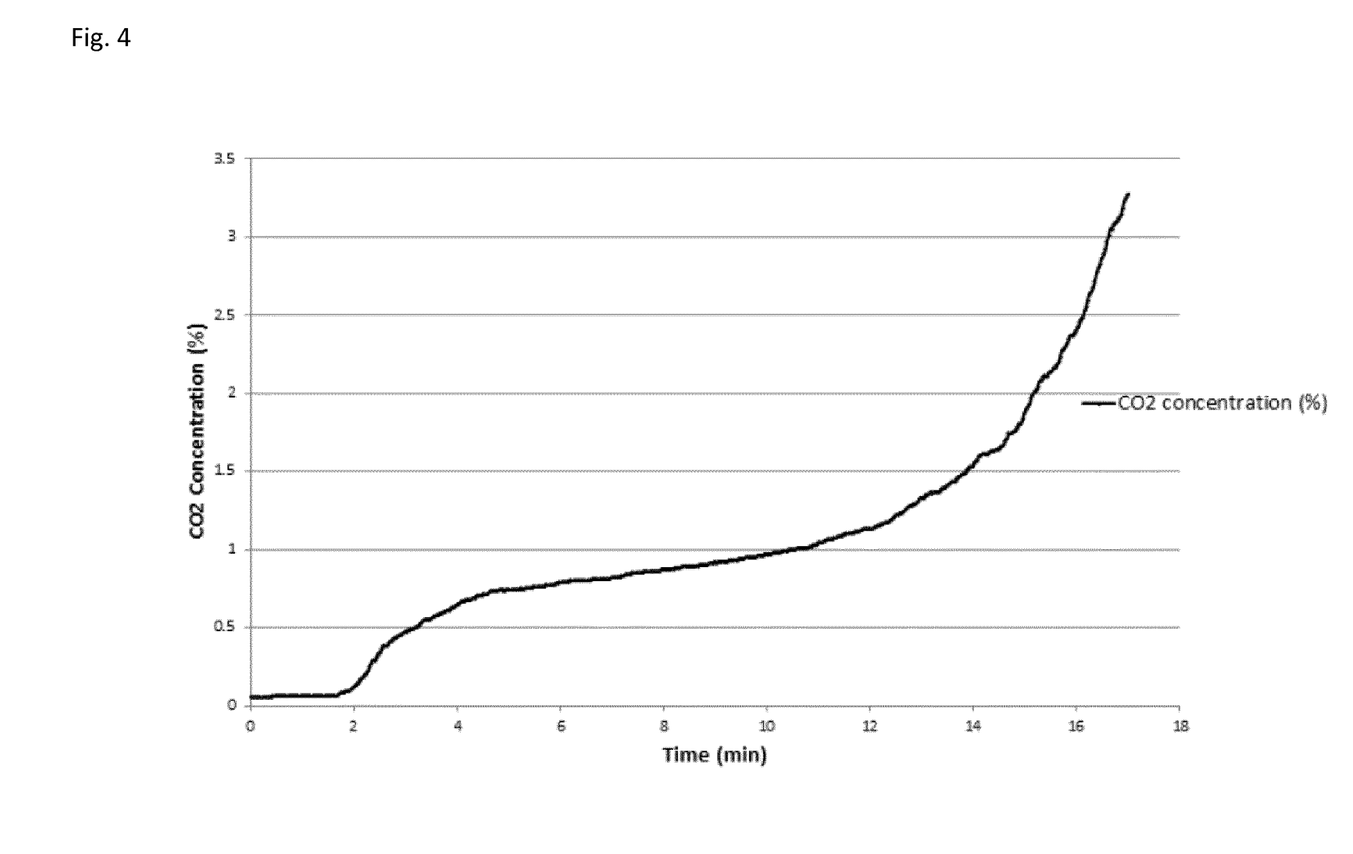
FIG. 4 shows $CO_2$ the desorption over time.

During this process the adsorbed $CO_2$ was released and the resulting $CO_2$-rich gas inside the container was pumped through a flow meter and a $CO_2$ sensor. Combining measurements from these components enabled the direct measurement of the quantity of $CO_2$ adsorbed by the material over the exposure period (see FIG. 4, showing the desorption over time, at a continuous flow rate of 1.0 l/min).

Table 2 discloses the adsorption of carbon dioxide, wherein the adsorption levels given as a percentage of [mass $CO_2$ adsorbed]/[dry mass sorbent material].

TABLE 2

$CO_2$ adsorption.

| Exposure Period [hours] | $CO_2$ captured [mass $CO_2$ adsorbed]/ [dry mass sorbent material] |
|---|---|
| 5 | 0.46 |
| 5 | 0.41 |
| 5 | 0.44 |
| >24 | 3.35 |

The container was then closed, and the adsorbed gas was removed via application of vacuum, while measuring the carbon dioxide concentration.

Summary of the Results

As described, the material cartridges can be exposed to the ambient air at a determined thickness that negates need for using pressurized gas in the capture process. The test proves adequate of adsorption of CO2 in this configuration by using a specialized set-up which exposes the material at a thickness of 10 mm.

EXAMPLE 2

Ambient Adsorption Test

Two rectangular cartridges having a dimensions of length by width of 10 cm, with an adsorbent bed thickness for cartridge 1 of 1 cm, and 5 cm for cartridge 2 by 20 cm (length by width by height). The cartridges comprised a stainless steel mesh, were loosely filled with a primary amino functional ion exchange resin, i.e. a divinyl benzene based polymeric particular adsorbent having a primary amino functionality at a total capacity of at least 2.0 eq./l, a surface area (BET) in the range of from 25 to 75 $m^2$/g, and an average pore diameter 5 to 150 nm). The test cartridges were placed in a vacuum oven with nitrogen purge (MSL) to remove all adsorbed carbon dioxide. Then the cartridges was taken from the vacuum oven and placed on a scale, thereby exposed to the ambient air. The weight gain was measured over time, and corrected for humidity. Carbon dioxide adsorption was measured by a Mettler Toledo mass balance/4 kg range (MSL), Sartorius BP310S mass balance/310 g range (MSL).

Figure 5:
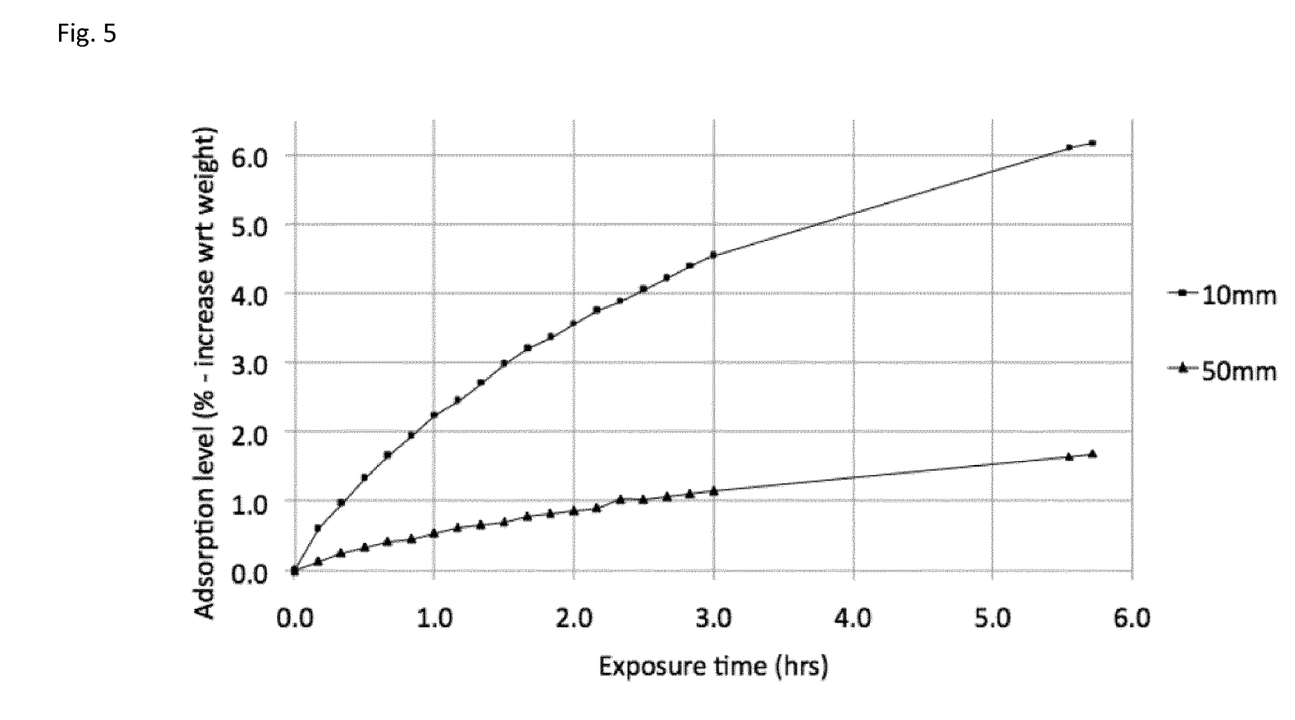
FIG. 5 shows the mass increase in % wt. of adsorbent in 1 and 5 cm thick cartridges at ambient conditions (22° C., 380 ppm $CO_2$, 45 humidity).

The result indicated that at a given wind speed, cartridge 1 showed a sufficiently high adsorption rate that permitted a sufficiently fast adsorption/desorption rate for an industrial process, whereas the additional adsorbent in cartridge 2 did not permit to increase the amount of carbon dioxide that could bead- and desorbed in this cycle, as illustrated in FIG. 5.

EXAMPLE 3

Electrically Heated Regeneration Arrangement

Figure 6:
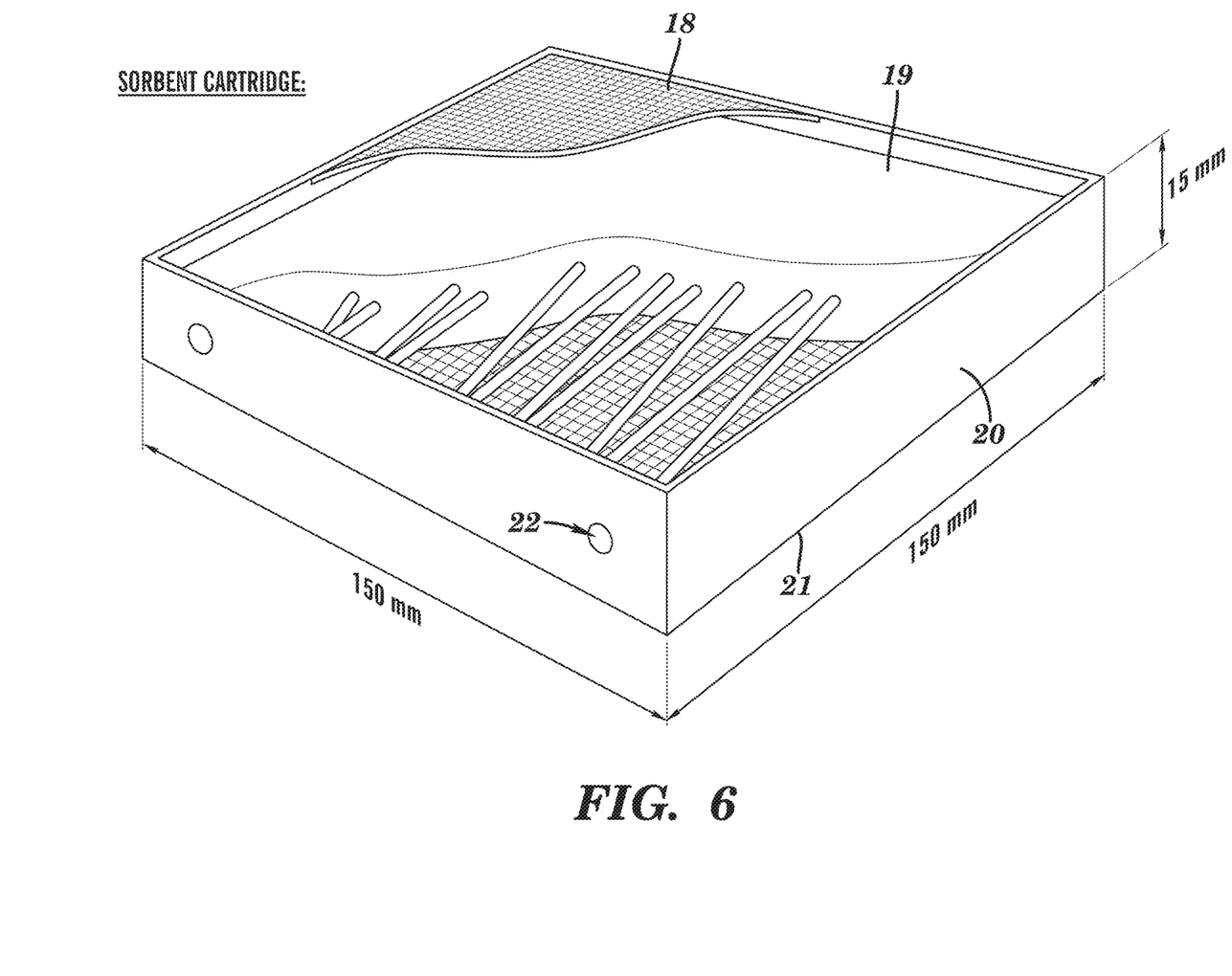
FIGS. 6 and 7 show schematically a preferred arrangement for use in an aquarium, with a single cartridge and electrical heating for the regeneration.

In a cartridge according to Example 2 having a volume of 100 $cm^3$, prior to loading with adsorbent material, a Nichrome wire, as typically used in hair dryers as heating means, of 40 cm length was embedded in a manner that allowed to heat the entirety of the content of the cartridge, by direct heat transfer to the adsorbent, which is in direct contact with the wire (see FIG. 6). The cartridge was then loaded with adsorbent. Applying less than 15 W of electricity to the wire allowed heating the entire cartridge to over 80° C. in less than 20 minutes.

The wire may be configured in differently ways to maximize heating efficiency based on the shape of the cartridge, ie. spirally in the case of a cylindrical volume.

EXAMPLE 4

Figure 7:
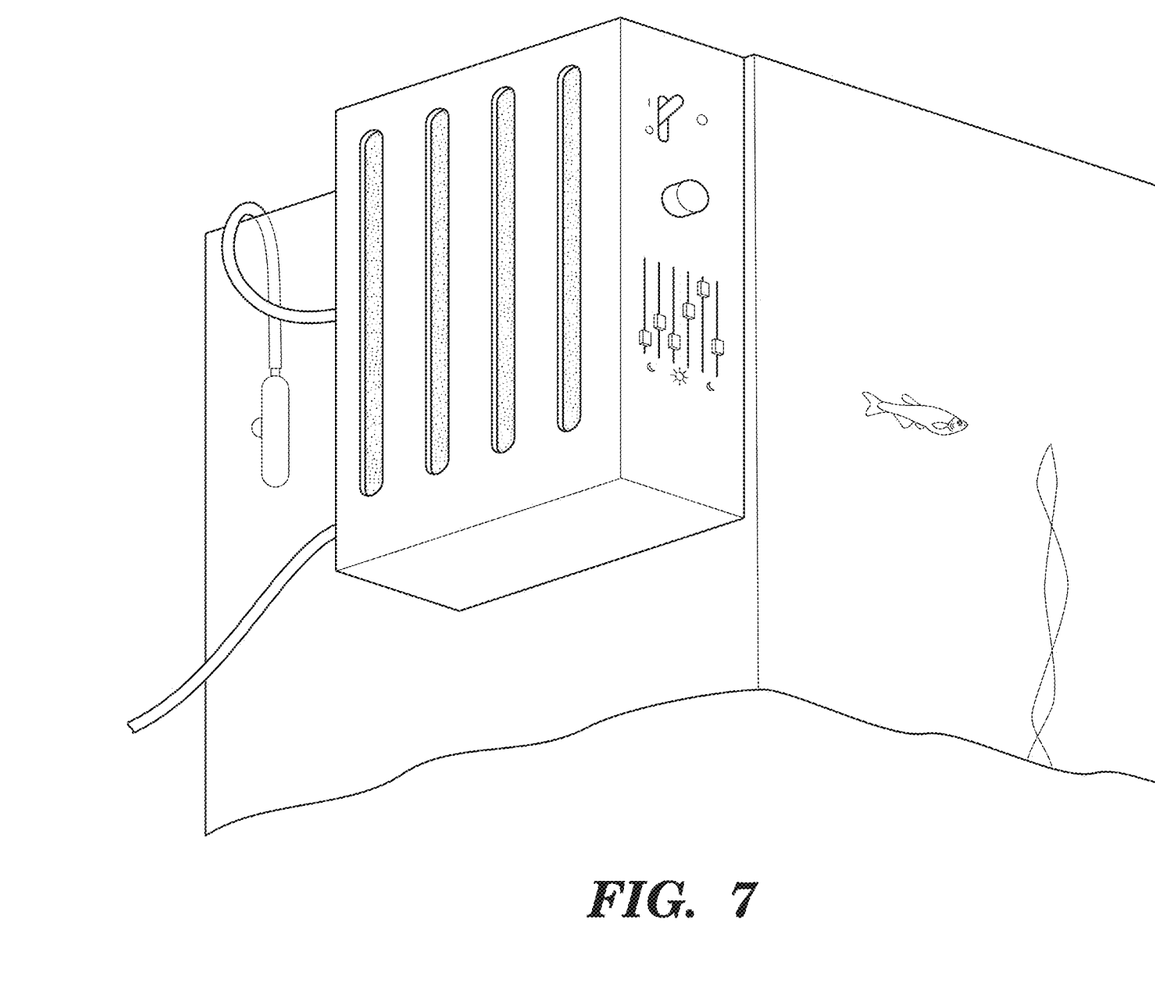
Figure 8:
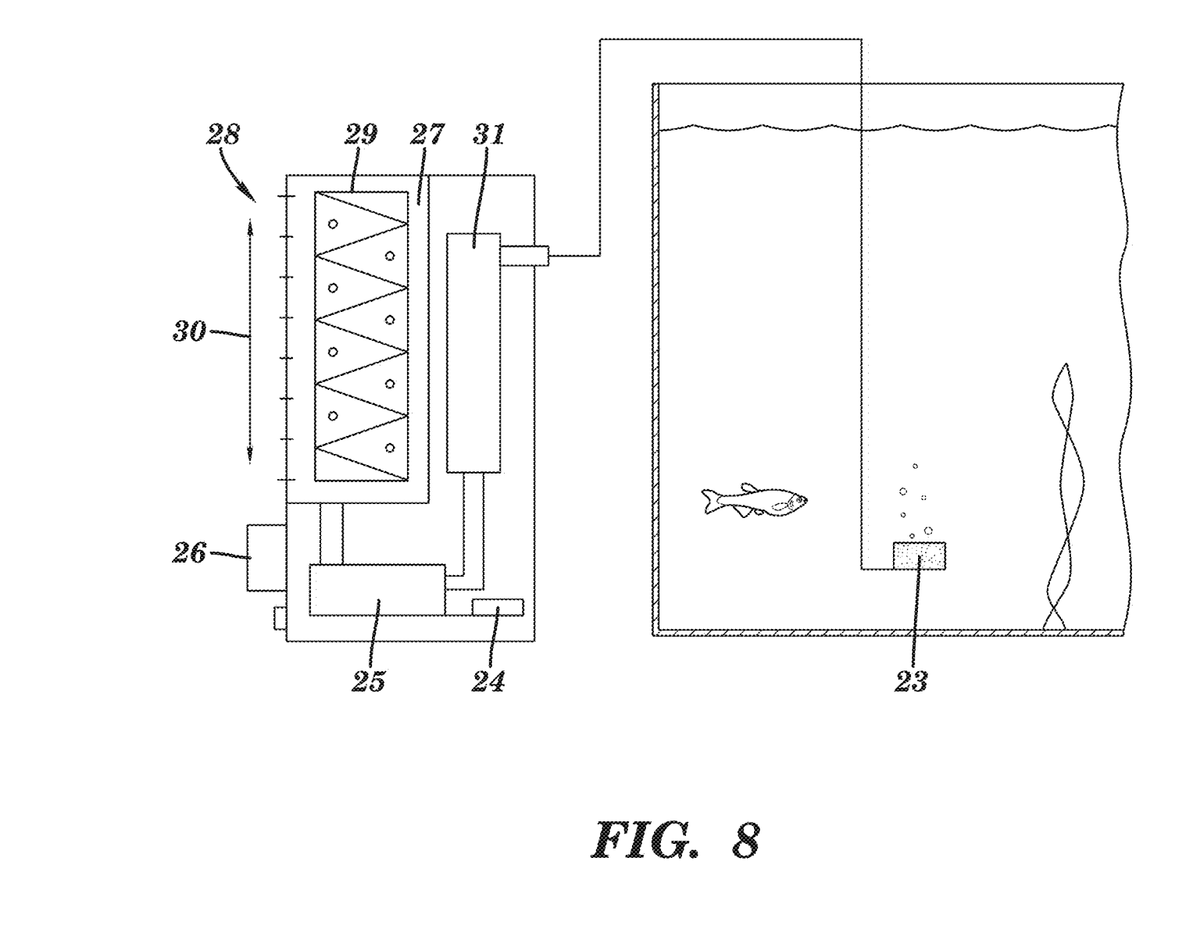
FIG. 8 shows a line up for use with an aquarium.

Aquarium $CO_2$ Air-Capture Arrangement Including Timer, Flow Control and Internet Connectivity (FIGS. 6 and 7)

A device was prepared comprising the cartridge of Example 3. The cartridge was allowed to come into contact with ambient air at atmospheric conditions. For circulation of the released carbon dioxide, a small pump was employed.

The device operates by intermittently heating the adsorbent cartridge which had been exposed to the room air where the aquarium was placed, relying entirely on natural diffusion of the carbon dioxide. For larger applications this may also comprise a means for air flow, such as a fan to speed up the adsorption process by increasing the overall amount of carbon dioxide that the adsorbent is exposed to in the same period.

After the adsorption period, the cartridge enclosure is then sealed using a sealing mechanism comprising an actuator, then heated up to 80° C. while a micro-pump is used to extract the released carbon dioxide into the aquarium through a ceramic sparger/diffuser. The pump was chosen to supply the slight overpressure needed to ensure homogenous gas distribution by the sparger, i.e. an overpressure of between 0.5 to 2.5 bar for the gas to get through.

The pump works either at a slow continuous rate, or at a faster rate at regular intermittencies, so as to avoid clear fluctuations in the $CO_2$ concentration in the water, to avoid stress to the living inhabitants of aquariums ie. the fish/shrimp/snails etc.

Alternatively a storage buffer for the $CO_2$ may be used from which the $CO_2$ is released gradually.

An advantage of the system is that additional functionality can be easily applied to the $CO_2$ supply device. For example, it will be easy to accurately adjust the flow rate of CO2 as this can be directly linked to the pump, ie. no continuous adjusting with a pressure regulator required to get to the right bubble count. In addition, a timer can easily integrated, without the need to buy an additional solenoid valve attached to the regulator. This is important because $CO_2$ is only required when incandescent light is available for the plants to perform photosynthesis. The system may further advantageously be remotely connected, e.g. through to the internet, to allow remote monitoring and controlling of the $CO_2$ supply, pH and other values, without the need to replace a gas cylinder.

Finally the system completely avoids the danger of 'end-of-tank' $CO_2$ dumps which can otherwise harm/kill the aquarium inhabitants.

The invention claimed is:
1. A device for the reversible adsorption of carbon dioxide from a gas mixture, comprising:
   at least one adsorbent vessel comprising one or a plurality of gas permeable cartridge vessels of an inert and dimensionally stable material, and each cartridge comprising a suitable polymeric particular adsorbent having only a primary amino functionality at a total capacity of at least 2.0 eq./l, a surface area (BET) in the range of from 25 to 75 $m^2$/g, and an average pore diameter of 1 to 200 nm; and further comprising:
a means for desorption of the adsorbed carbon dioxide by pressure, humidity, or temperature adsorption swing, or both;
a means for directing the desorbed gas mixture from the adsorbent cartridges;
a means for the supplying the gas mixture to the cartridges;
a means for recuperation of heat or fluids or heat and fluids, and a desorbed gas mixture;
at least one of:
a means for measuring the carbon dioxide adsorption level, a means for measuring carbon dioxide gas flow rates, and a means for contacting the adsorbent with a warm fluid for inducing desorption of the carbon dioxide; and
an arrangement to subject the cartridges to reduced pressure, and subsequently to contact the cartridges with water having a temperature in the range of from 60° C. to 100° C., and a means for separating water or water vapour from the released carbon dioxide for recycling to arrangement.

2. The device according to claim 1, wherein the cartridge vessels comprise a gas permeable membrane with an average pore diameter in the range of from 0.01-0.25 mm.

3. The device according to claim 1, wherein the shape and thickness of the cartridges is determined by allowing for an adsorption-desorption regeneration cycle of between 2 and 24 hours.

4. The device according to claim 1, wherein one or more cartridges are arranged sequentially or parallel, or sequentially and parallel such that one or more cartridges can be removed for replacement or maintenance without having to stop the adsorption process or without forcing the dismantling of the capture unit.

5. The device according to claim 1, further comprising a storage buffer.

6. The device according to claim 5, wherein the storage buffer has a storage volume equivalent to an amount of carbon dioxide enriched gas mixture as required for of from 0.1 to 2 days $CO_2$ usage for a particular application.

7. The device according to claim 1, for the provision of a carbon dioxide enriched gas stream to an aquarium, further comprising a means for a subsequent desorption of the adsorbed carbon dioxide to form a carbon dioxide enriched gas stream, and a means for the supply of the carbon dioxide enriched gas stream to an aquarium, to form at least in part dissolved carbon dioxide.

8. The device according to claim 1, further comprising a means for heating the saturated adsorbent electrically.

9. The device according to claim 5, wherein the storage buffer holds the carbon dioxide in any one or more of: a compressed form, a solid storage structure comprising activated carbon or a metal organic framework.

10. An arrangement for any of: the enhancement of plant growth, beverage carbonation, pH control and storage of perishable goods, the arrangement comprising the device according to claim 1, and further comprising a means for distributing the desorbed carbon dioxide, wherein the means is any one or more of: gas duct, pump or a sparger.

11. The arrangement according to claim 10, further comprising at least one of: a greenhouse for increasing plant growth, a vivarium, an aquarium, or a photo bioreactor for microalgae growth.

12. The arrangement according to claim 11, further comprising a low energy grade provision means, wherein a low grade energy provision means is provided by electrical heating for heating the absorbent in a cartridge through direct contact with a heating means to a temperature of from 60° C. to 150° C.

13. An arrangement for the enhancement of plant growth in aquaria, comprising the device according to claim 1, and further comprising a means for distributing the desorbed carbon dioxide, wherein the distributing means is any one or more of: a gas duct, or a sparger.

14. A process for separating carbon dioxide from a gas mixture by a temperature and humidity swing adsorption-desorption process, or a temperature or humidity swing adsorption-desorption process, the process comprising the steps of:
(a) in the device according to claim 1, contacting the gas mixture with the adsorbent at a pressure $P_1$, a humidity $H_1$ and a temperature $T_1$ until a desired amount of carbon dioxide is adsorbed onto the adsorbent, and
(b) desorbing at least part of the carbon dioxide adsorbed in step (a), to produce a stream enriched in carbon dioxide at a total pressure $P_2$ or a temperature $T_2$, or both, at which temperature the carbon dioxide has a lower adsorption constant with respect to the adsorbent and therefore at least in part desorbs.

15. The process according to claim 14, wherein step (b) includes contacting the one or more cartridges with a fluid at a temperature in the range of from 60° C. to 150° C., or heating the adsorbent in a cartridge through direct contact with a heating means to a temperature of from 60° C. to 150° C., or both.

16. The process according to claim 14, wherein the contacting or heating, or both, is done at a reduced pressure.

17. The process according to claim 14, comprising alternating steps (a) and (b) in a pattern of between 0.1 minutes and 48 hours.

18. The process according to claim 14, comprising reversing the flow of the gas mixture for step (b) and increasing the temperature.

19. The process according to claim 14, further comprising: (c) directing the released gaseous stream comprising the desorbed carbon dioxide to a desired application comprising any one or more of: a green house, a (micro) algae photo incubator, a beverage plant, a vivarium, an aquarium, or a storage facility, wherein the released gaseous carbon dioxide is at least in part directed towards a carbon dioxide storage buffer.

20. The process according to claim 19, wherein the released gaseous carbon dioxide is at least in part sparged through an aqueous medium.

21. The process according to claim 14, wherein the carbon dioxide is released in a continuous or sequential manner.

22. Use of a device for the provision of carbon dioxide to aquaria, or for the provision of carbon dioxide to control the pH of an aqueous medium, the device comprising:
at least one adsorbent vessel comprising one or a plurality of gas permeable cartridge vessels of an inert and dimensionally stable material, and each cartridge comprising a suitable polymeric particular adsorbent having only a primary amino functionality at a total capacity of at least 2.0 eq./l, a surface area (BET) in the range of from 25 to 75 m²/g, and an average pore diameter of 1 to 200 nm; and
further comprising:
a means for desorption of the adsorbed carbon dioxide by pressure, humidity, or temperature adsorption swing, or both; and
a means for directing the desorbed gas mixture from the adsorbent cartridges.

23. Use of an arrangement for the provision of carbon dioxide to aquaria, or for the provision of carbon dioxide to control the pH of an aqueous medium, the arrangement comprising:
- i) a device comprising:
    - at least one adsorbent vessel comprising one or a plurality of gas permeable cartridge vessels of an inert and dimensionally stable material, and each cartridge comprising a suitable polymeric particular adsorbent having only a primary amino functionality at a total capacity of at least 2.0 eq./l, a surface area (BET) in the range of from 25 to 75 $m^2/g$, and an average pore diameter of 1 to 200 nm; and
- further comprising:
    - a means for desorption of the adsorbed carbon dioxide by pressure, humidity, or temperature adsorption swing, or both; and
    - a means for directing the desorbed gas mixture from the adsorbent cartridges,
- ii) a means for distributing the desorbed carbon dioxide, wherein the means is any one or more of: gas duct, pump or a sparger.

* * * * *